(12) United States Patent
Pei

(10) Patent No.: US 6,372,881 B2
(45) Date of Patent: Apr. 16, 2002

(54) MONOMERS FOR PREPARING ARYLAMINE-SUBSTITUTED POLY (ARYLENE-VINYLENES)

(75) Inventor: Qibing Pei, Fremont, CA (US)

(73) Assignee: SRI International, Menlo Park, CA (US)

( * ) Notice: Subject to any disclaimer, the term of this patent is extended or adjusted under 35 U.S.C. 154(b) by 0 days.

(21) Appl. No.: 09/912,927

(22) Filed: Jul. 24, 2001

Related U.S. Application Data

(62) Division of application No. 09/619,372, filed on Jul. 19, 2000.
(60) Provisional application No. 60/144,938, filed on Jul. 20, 1999.

(51) Int. Cl.⁷ .......................... C08G 61/00; C08G 12/02
(52) U.S. Cl. .......................... 528/397; 528/230; 528/86; 528/211; 528/422; 544/1; 428/690; 428/917; 525/242
(58) Field of Search ............................ 525/242; 528/86, 528/211, 230, 397, 422; 544/1; 428/690, 917

(56) References Cited

U.S. PATENT DOCUMENTS

| | | |
|---|---|---|
| 4,395,475 A | 7/1983 | Noonan et al. |
| 4,801,517 A | 1/1989 | Frechet et al. |
| 4,818,650 A | 4/1989 | Limburg et al. |
| 5,189,136 A | 2/1993 | Wudl et al. |

(List continued on next page.)

FOREIGN PATENT DOCUMENTS

| | | |
|---|---|---|
| EP | 0376311 | 7/1990 |
| WO | WO 98/27136 | 6/1998 |
| WO | WO 99/21936 | 5/1999 |

OTHER PUBLICATIONS

Kraft et al. (1998), "Electroluminescent Conjugated Polymers—Seeing Polymers in a New Light," *Agnew. Chem. Int. Ed.* 37:403–428.

Rost et al. (1997), "Novel Light Emitting and Photoconducting Polyarylenevinylene Derivatives Containing Phenylene Arylamine and Phenylene Oxide Units in the Main Chain," *Synthetic Metals* 84:269–270.

(List continued on next page.)

*Primary Examiner*—Duc Truong
(74) *Attorney, Agent, or Firm*—Diane E. Reed; Reed & Associates

(57) ABSTRACT

The invention provides novel conjugated polymers comprised of arylamine-substituted poly(arylene vinylenes). The polymers have the general structure (I)

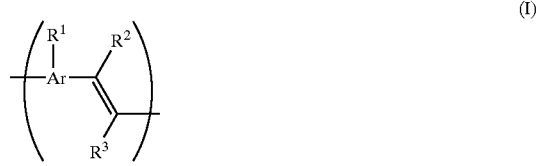

wherein: Ar is arylene, heteroarylene, substituted arylene or substituted heteroarylene containing one to three aromatic rings; $R^1$ is an arylamine substituent having the formula $-Ar^1-N(R^4R^5)$ wherein $Ar^1$ is as defined for Ar and $R^4$ and $R^5$ are independently hydrocarbyl, substituted hydrocarbyl, heteroatom-containing hydrocarbyl, or substituted heteroatom-containing hydrocarbyl, or together form a cyclic group; and $R^2$ and $R^3$ are independently selected from the group consisting of hydrido, halo and cyano, or may be as defined for $R^4$ and $R^5$, or may together form a triple bond. Monomeric precursors and methods of synthesizing the precursors are also provided, as are electroluminescence and other devices containing a polymer of the invention.

16 Claims, 5 Drawing Sheets

U.S. PATENT DOCUMENTS

| | | |
|---|---|---|
| 5,247,190 A | 9/1993 | Friend et al. |
| 5,389,444 A | 2/1995 | Hosokawa et al. |
| 5,534,613 A | 7/1996 | Tan et al. |
| 5,536,866 A | 7/1996 | Tan et al. |
| 5,558,904 A | 9/1996 | Hsieh et al. |
| 5,604,292 A | 2/1997 | Stenger-Smith et al. |
| 5,682,043 A | 10/1997 | Pei et al. |
| 5,726,457 A | 3/1998 | Nakano et al. |
| 5,814,244 A | 9/1998 | Kreuder et al. |
| 5,895,717 A | 4/1999 | Cao et al. |
| 5,900,327 A | 5/1999 | Pei et al. |

OTHER PUBLICATIONS

Stenger–Smith et al. (1998), "Synthesis and Characterization of Poly(2,5–Bis(N–Methyl–N–Hexylamino)Phenylene Vinylene), a Conjugated Polymer for Light–Emitting Diodes," *Macromolecules* 31:7566–7569.

MONOMERS FOR PREPARING ARYLAMINE-SUBSTITUTED POLY (ARYLENE-VINYLENES)

CROSS-REFERENCE TO RELATED APPLICATIONS

This is a divisional of U.S. patent application Ser. No. 09/619,372, filed Jul. 19, 2000 now allowed, which claims priority under 35 U.S.C. §119(e)(1) to U.S. Provisional Patent Application Ser. No. 60/144,938, filed Jul. 20, 1999, the disclosures of which are incorporated by reference herein.

TECHNICAL FIELD

This invention relates generally to the field of conjugated polymers, and more particularly relates to a novel class of conjugated polymers useful as semiconductive materials in electroluminescent devices and the like.

BACKGROUND

"Conjugated" polymers are polymers having a π-electron conjugated system along the main chain (or "backbone"), and have been known for some time to have utility as organic semiconducting materials. See, e.g., *Organic Conductors*, ch. 11, J.P. Farger, Ed. (New York, N.Y.: Marcel Dekker, 1994). Conjugated polymers include, for example, cis and trans polyacetylenes, polydiacetylenes, polyparaphenylenes, polypyrroles, polythiophenes, polybithiophenes, polyisothianaphthene, polyphenylenevinylenes, polythienylvinylenes, polyphenylenesulfide, and polyaniline. More recently, conjugated polymers have also been discovered to be useful as electroluminescent materials, i.e., as materials that emit light when excited by application of an electric current (Burroughs et al. (1990) *Nature* 347:539–541; May (1995) *Phys. World* 8(3):52–57). Accordingly, these polymers have been proposed for use in a variety of applications. For example, conjugated polymers may be used as the active material in semiconductor thin film devices such as light emitting diodes (LEDs), transistors, photodetectors and solar cells. Conjugated polymers may also be used in electrochemical devices such as rechargeable batteries and light emitting electrochemical cells (both as thin films and in solution), as electrochemical sensors, and as electrical conductors (after being heavily doped).

Poly(p-phenylene vinylene) ("PPV") is a conjugated polymer of particular interest because of its simplicity and cost; the polymer is also advantageous in terms of processability and tensile properties; see Kraft et al. (1998) *Angew. Chem. Int.* Ed. 37:402–428.

POLY(*p*-PHENYLENE VINYLENE)

Like other conjugated polymers, PPV is insoluble in most organic solvents, including those used in silicon microfabrication technology. Some soluble PPV derivatives have been prepared by covalent attachment of flexible side groups or segments; such derivatives include poly (2-methoxy-5-(2-ethylhexyloxy)-1,4-phenylene vinylene ("MEH-PPV") (see U.S. Pat. No. 5,189,136 to Wudl et al.) and poly (2,5-bischelostanoxy-1,4-phenylene vinylene) ("BCHA-PPV") (e.g., as described in International Patent Publication No. WO 98/27136), which are soluble in common solvents such as toluene, tetrahydrofuran, xylene and chloroform. However, these side groups are electronically passivative, and considerably reduce the semiconductivity of the conjugated polymer by separating polymer chains from each other and consequently hindering charge mobility between polymer chains. U.S. Pat. No. 5,604,292 to Stenger-Smith et al. is also of interest insofar as the patent pertains to a PPV derivative, i.e., poly(2-N,N-dimethylamino phenylene vinylene), but that polymer as well is limited in terms of electroluminescence.

There is accordingly a need in the art for conjugated semiconductive polymers that are soluble in common organic solvents, particularly those used in semiconductor processing, but nevertheless retain semiconductivity, photoluminescent and electroluminescent efficiency, tensile strength, and thermal, chemical and photochemical stability.

SUMMARY OF THE INVENTION

The present invention is addressed to the aforementioned need in the art, and provides a novel family of conjugated semiconductive polymers useful in a variety of applications, including fabrication of semiconductor thin film devices (e.g., LEDs, transistors, photodetectors and solar cells) and electrochemical devices (e.g., rechargeable batteries, light-emitting electrochemical cells, and electrochemical sensors).

It is another object of the invention to provide such conjugated semiconductive polymers in the form of poly (arylene vinylenes) wherein some or all of the backbone arylene units are substituted with an arylamine functionality.

It is still another object of the invention to provide such conjugated semiconductive polymers wherein the substituted poly(arylene vinylene) is poly(P-phenylene vinylene) or a derivative or analog thereof.

It is yet another object of the invention to provide an arylamine-substituted monomer useful for preparing the aforementioned conjugated polymers.

It is an additional object of the invention to provide electroluminescence devices containing a polymer of the invention as the electroluminescent material.

It is a further object of the invention to provide other types of semiconductor thin film devices and electrochemical devices fabricated with a polymer of the invention.

Additional objects, advantages and novel features of the invention will be set forth in part in the description which follows, and in part will become apparent to those skilled in the art upon examination of the following, or may be learned by practice of the invention.

In one embodiment, then, new conjugated polymers are provided in the form of arylamine-substituted poly(arylene vinylenes) containing monomer units having the general structure of formula (I)

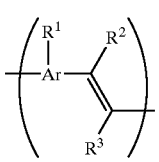

(I)

wherein: Ar is arylene, heteroarylene, substituted arylene or substituted heteroarylene containing one to three aromatic rings; $R^1$ is an arylamine substituent having the formula —Ar$^1$—N(R$^4$R$^5$) wherein Ar$^1$ is as defined for Ar and R$^4$ and R$^5$ are independently hydrocarbyl, substituted hydrocarbyl, heteroatom-containing hydrocarbyl, or substituted heteroatom-containing hydrocarbyl, or R$^4$ and R$^5$ can together form a cyclic group; and R$^2$ and R$^3$ are independently selected from the group consisting of hydrido, halo and cyano, or may be as defined for R$^4$ and R$^5$, or may together form a triple bond.

In another embodiment, novel monomers are provided that are useful for synthesizing the aforementioned polymers, the monomers having the general structure (VI)

(VI)

wherein: Ar and R$^1$ are as defined previously, and L$^1$ and L$^2$ are selected from the group consisting of —CHO, —Br, —I and —CH$_2$—L wherein L is a reactive group (e.g., a leaving group) that enables reaction with like monomers (i.e., also having the structure of formula (VI)) and/or with vinyl monomers.

In a further embodiment, electroluminescence devices are provided that contain a polymer of the invention as the electroluminescent materials. These devices include light-emitting diodes (LEDs), photodetector devices, and light-emitting electrochemical cells. In a particularly preferred embodiment, an electroluminescence device prepared with a polymer of the invention is a cavity-emission electroluminescence device.

In an additional embodiment, other types of devices are provided that are fabricated with a polymer of the invention, particularly photovoltaic devices used for the generation of electrical power, electrochemical sensors used for detecting and/or quantitating chemical and/or biological materials, and transistors, e.g., field-effect transistors (FETs).

Figure 1:
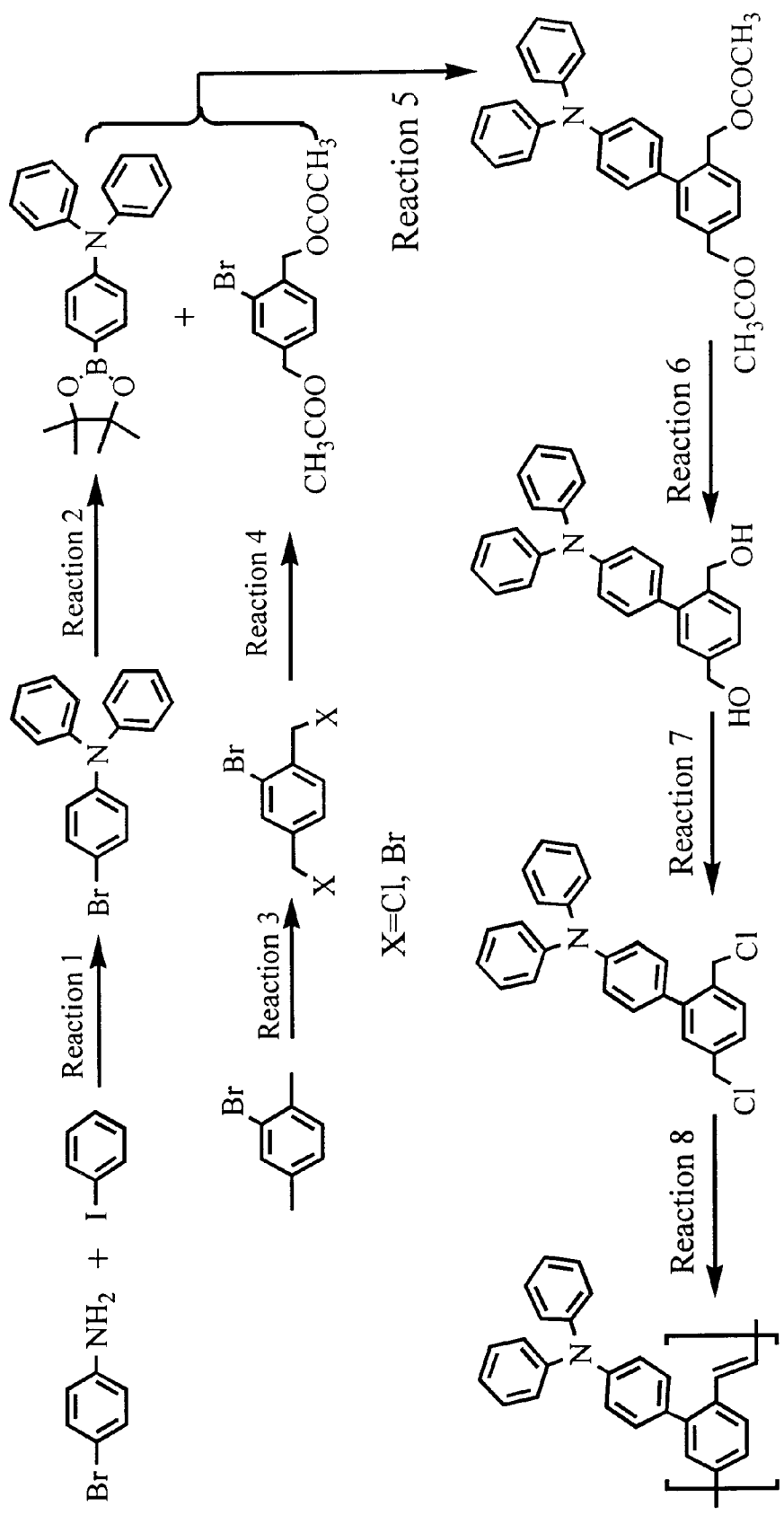
FIG. 1 schematically illustrates the preparation of the monomeric precursor 1,4-bis(chloromethyl)-2-(4-diphenylarninophenyl)benzene as described in Example 1, followed by polymerization to give poly(2-(4-diphenylaminophenyl)-1,4-phenylene vinylene as described in Example 2.

DETAILED DESCRIPTION OF THE INVENTION
DEFINITIONS AND OVERVIEW

It is to be understood that unless otherwise indicated, this invention is not limited to specific starting materials, reagents or reaction conditions, as such may vary. It is also to be understood that the terminology used herein is for the purpose of describing particular embodiments only and is not intended to be limiting.

As used in this specification and the appended claims, the singular forms "a," "an" and "the" include plural referents unless the context clearly dictates otherwise. Thus, reference to reference to "a monomer unit" includes combinations of different monomer units, "a polymer" includes mixtures of different polymers, and the like.

As used herein, the phrase "having the structure" is not intended to be limiting and is used in the same way that the term "comprising" is commonly used. The term "independently selected from the group consisting of" is used herein to indicate that the recited elements, e.g., R groups or the like, can be identical or different.

"Optional" or "optionally" means that the subsequently described event or circumstance may or may not occur, and that the description includes instances where said event or circumstance occurs and instances where it does not. For example, the phrase "optionally substituted aryl" means that an aryl moiety may or may not be substituted and that the description includes both unsubstituted aryl and aryl where there is substitution.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, 2-ethylhexyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of one to six carbon atoms, preferably one to four carbon atoms. "Substituted alkyl" refers to alkyl substituted with one or more substituent groups, and the terms "heteroatom-containing alkyl" and "heteroalkyl" refer to alkyl in which at least one carbon atom is replaced with a heteroatom.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing one to six, more preferably one to four, carbon atoms.

The term "aryl" as used herein, and unless otherwise specified, refers to a univalent aromatic substituent containing a single aromatic ring or multiple aromatic rings that are fused together or linked covalently. Preferred aryl groups contain one aromatic ring or two fused or linked aromatic rings, e.g., phenyl, naphthyl, biphenyl, fluorenyl, and the like. "Substituted aryl" refers to an aryl moiety substituted with one or more substituent groups, and the terms "heteroatom-containing aryl" and "heteroaryl" refer to aryl in which at least one carbon atom is replaced with a heteroatom.

The term "arylene" as used herein, and unless otherwise specified, refers to a divalent aromatic substituent containing a single aromatic ring or multiple aromatic rings that are fused together or linked covalently. Preferred arylene groups contain one aromatic ring or two fused or linked aromatic rings. "Substituted arylene" refers to an arylene moiety substituted with one or more substituent groups, and the terms "heteroatom-containing arylene" and "heteroarylene" refer to arylene in which at least one carbon atom is replaced with a heteroatom.

The term "aralkyl" refers to an alkyl group with an aryl substituent, and the term "aralkylene" refers to an alkylene group with an aryl substituent; the term "alkaryl" refers to an aryl group that has an alkyl substituent, and the term "alkarylene" refers to an arylene group with an alkyl substituent.

The terms "halo" and "halogen" are used in the conventional sense to refer to a chloro, bromo, fluoro or iodo substituent. The terms "haloalkyl," "haloalkenyl" or "haloalkenyl" (or "halogenated alkyl," "halogenated alkenyl," "halogenated aromatic" or "halogenated alkynyl") refers to an alkyl, alkenyl, aromatic or alkynyl group, respectively, in which at least one of the hydrogen atoms in the group has been replaced with a halogen atom.

The term "heteroatom-containing" refers to a molecule or molecular fragment in which one or more carbon atoms is replaced with an atom other than carbon, e.g., nitrogen, oxygen, sulfur, phosphorus or silicon. Similarly, the term "heteroalkyl" refers to an alkyl substituent that is heteroatom-containing, the term "heterocyclic" refers to a cyclic substituent that is heteroatom-containing, the term "heteroaryl" refers to an aryl substituent that is heteroatom-containing, and the like.

"Hydrocarbyl" refers to univalent hydrocarbyl radicals containing 1 to about 30 carbon atoms, preferably 1 to about 24 carbon atoms, most preferably 1 to about 12 carbon atoms, including branched or unbranched, saturated or unsaturated species, such as alkyl groups, alkenyl groups, aryl groups, and the like. The term "lower hydrocarbyl" intends a hydrocarbyl group of one to six carbon atoms, preferably one to four carbon atoms. The term "hydrocarbylene" intends a divalent hydrocarbyl moiety containing 1 to about 30 carbon atoms, preferably 1 to about 24 carbon atoms, most preferably 1 to about 12 carbon atoms, including branched or unbranched, saturated or unsaturated species, or the like. The term "lower hydrocarbylene" intends a hydrocarbylene group of one to six carbon atoms, preferably one to four carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom.

A "Lewis acid" refers to any species with a vacant orbital, in contrast to a "Lewis base," which refers to a compound with an available pair of electrons, either unshared or in π-orbital. Typically, a Lewis acid refers to a compound containing an element that is two electrons short of having a complete valence shell.

The term "polyether" as in a "polyether substituent" refers to the moiety —(CH$_2$)$_m$(OCH$_2$CH$_2$)$_p$OR wherein m is zero, 1 or 2, p is generally 1 to 12, preferably 1 to 6, most preferably 1 to 3, and R is alkyl, preferably lower alkyl such as methyl or ethyl By "substituted" as in "substituted hydrocarbyl," "substituted hydrocarbylene," "substituted alkyl," "substituted alkenyl" and the like, as alluded to in some of the aforementioned definitions, is meant that in the hydrocarbyl, hydrocarbylene, alkyl, alkenyl or other moiety, at least one hydrogen atom bound to a carbon atom is replaced with one or more substituents that are functional groups such as hydroxyl, alkoxy, thio, amino, halo, silyl, and the like. When the term "substituted" appears prior to a list of possible substituted groups, it is intended that the term apply to every member of that group. That is, the phrase "substituted alkyl, alkenyl and alkynyl" is to be interpreted as "substituted alkyl, substituted alkenyl and substituted alkynyl."Similarly, "optionally substituted alkyl, alkenyl and alkynyl" is to be interpreted as "optionally substituted alkyl, optionally substituted alkenyl and optionally substituted alkynyl."

THE NOVEL POLYMERS

The polymers of the invention are conjugated semiconductive polymers in the form of poly(arylene vinylenes) wherein some or all of the backbone arylene units are substituted with an arylamine functionality. The polymers have the general structure of formula (I)

(I)

wherein:

Ar is arylene, heteroarylene, substituted arylene or substituted heteroarylene containing one to three aromatic rings;

R$^1$ is the arylamine substituent and is of the formula —Ar$^1$—N(R$^4$R$^5$) wherein Ar$^1$ is as defined for Ar and R$^4$ and R$^5$ are independently hydrocarbyl, substituted hydrocarbyl, heteroatom-containing hydrocarbyl, or substituted heteroatom-containing hydrocarbyl, or R$^4$ and R$^5$ can together form a cyclic group; and R$^2$ and R$^3$ are independently selected from the group consisting of hydrido, halo, cyano, hydrocarbyl, substituted hydrocarbyl, heteroatom-containing hydrocarbyl, and substituted heteroatom-containing hydrocarbyl, or R$^2$ and R$^3$ may together form a triple bond.

Preferred moieties are as follows:

Ar may be a five-membered or six-membered arylene, heteroarylene, substituted arylene or substituted heteroarylene group, or may contain one to three such groups, either fused or linked. Preferably, Ar is comprised of one or two aromatic rings, and is most preferably comprised of a single aromatic ring that is five-membered or six-membered arylene, heteroarylene, substituted arylene or substituted heteroarylene. Ar$_1$, the arylene linking moiety in the arylamine substituent, is defined in the same way. Examples of suitable Ar and Ar$^1$ moieties include, but are not limited to, the following:

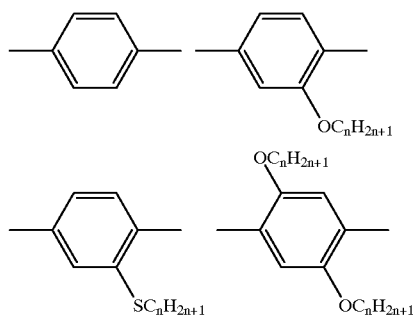

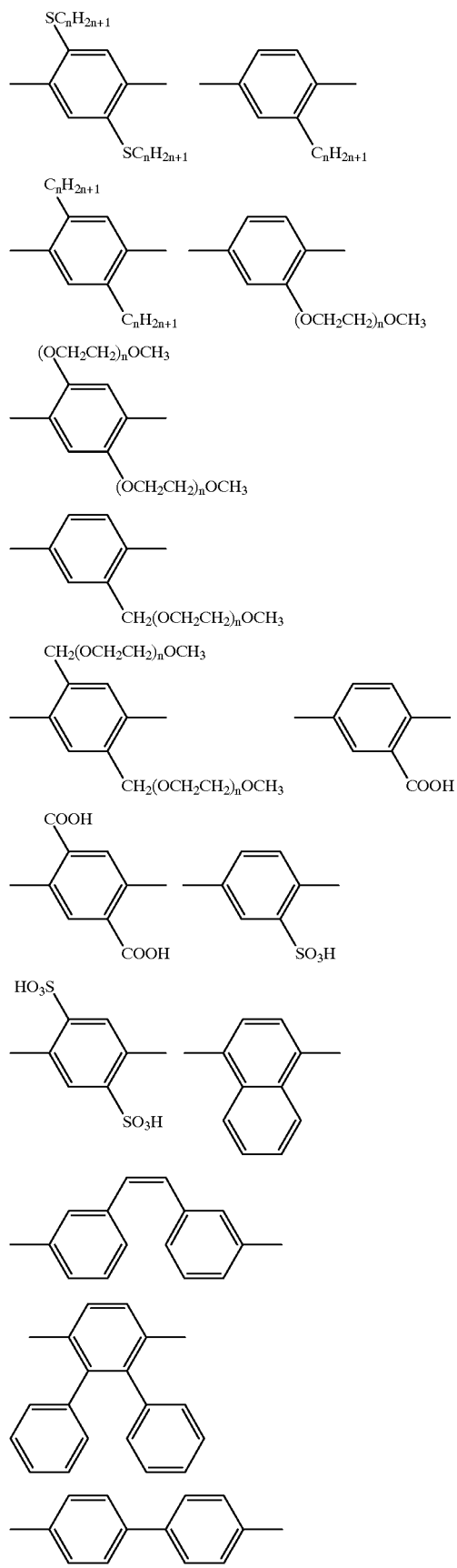
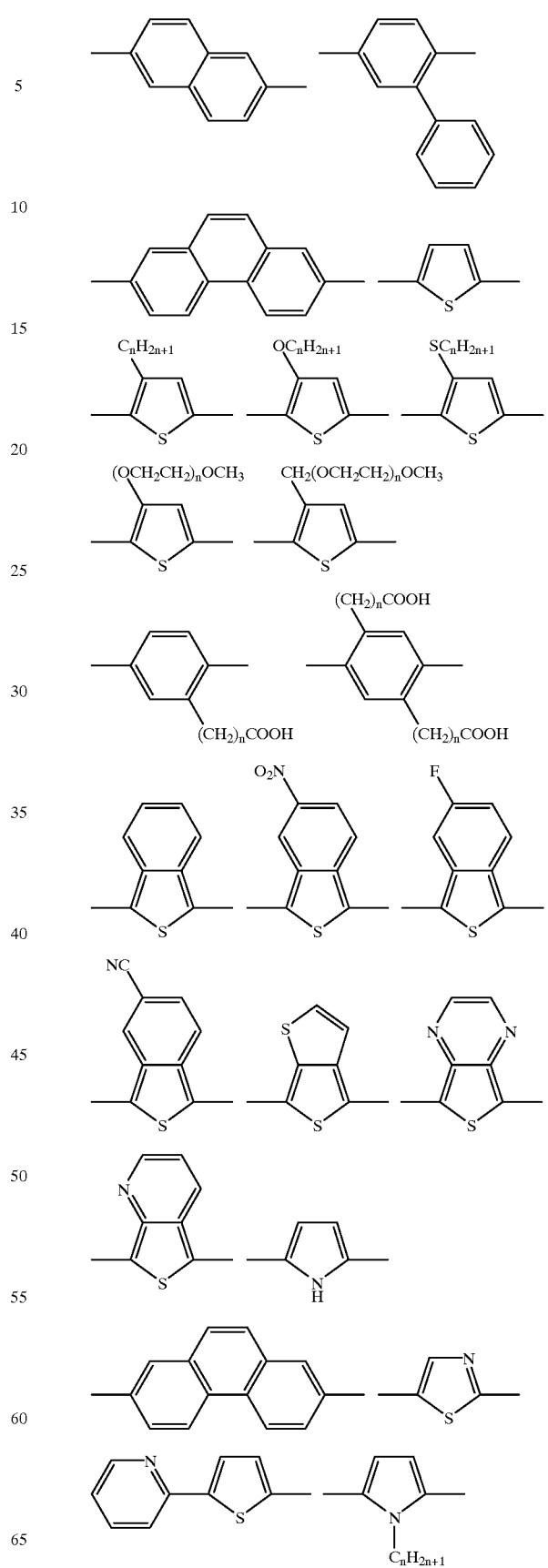

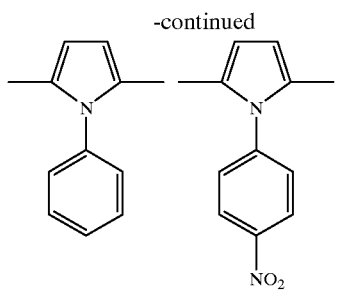

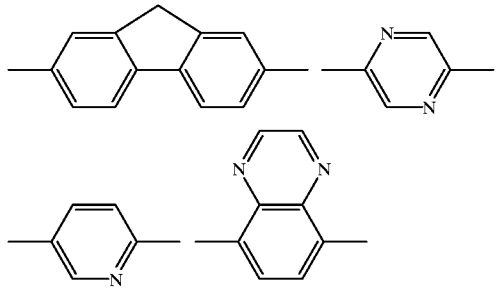

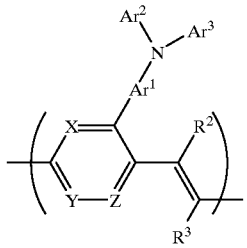

In the above structures, n is generally in the range of 1 to 12 inclusive.

The substituents $R^2$ and $R^3$ are generally hydrido but may also be halo (particularly chloro or fluoro) or cyano, or substituted or unsubstituted alkyl, alkoxy, alkenyl, alkynyl, aryl and heteroaryl. Alternatively, $R^2$ and $R^3$ together form an additional bond, such that a triple bond connects the two carbon atoms shown. In a particularly preferred embodiment, $R^2$ and $R^3$ are hydrido or cyano, or together form a triple bond.

$R^4$ and $R^5$ may be the same or different and, as noted, are hydrocarbyl, substituted hydrocarbyl, heteroatom-containing hydrocarbyl, or substituted heteroatom-containing hydrocarbyl, or $R^4$ and $R^5$ may together form a cyclic group, typically a non-aromatic ring that may or may not be substituted with one or more, typically one or two, preferably one heteroatom, and preferably a five- or six-membered ring or a crown ether. For example, $R^4$ and $R^5$ may be alkyl, alkoxy-substituted alkyl, polyether-substituted alkyl, cyano-substituted alkyl, halo substituted alkyl, aryl, alkoxy-substituted aryl, polyether-substituted aryl, cyano-substituted aryl, halo-substituted aryl, alkyl-substituted aryl, heteroaryl, alkoxy-substituted heteroaryl, polyether-substituted heteroaryl, nitro-substituted heteroaryl, halo-substituted heteroaryl, and the like, or $R^4$ and $R^5$ may together form a piperidinyl, piperazinyl, morpholinyl, or pyrrolidinyl ring. Particularly preferred substituents are aryl, e.g., phenyl, alkoxy-substituted phenyl (particularly lower alkoxy-substituted phenyl such as methoxyphenyl), polyether-substituted phenyl (particularly phenyl substituted with a —$(CH_2)_m(OCH_2CH_2)_p$OR group wherein m is zero, 1 or 2, p is generally 1 to 12, preferably 1 to 6, most preferably 1 to 3, and R is alkyl, preferably lower alkyl such as methyl or ethyl), alkyl-substituted phenyl (particularly lower alkyl-substituted phenyl), and halo-substituted phenyl (particularly fluorinated or chlorinated phenyl).

In a preferred embodiment, the arylamine-substituted arylene-vinylene polymer contains monomer units having the general structure of formula (II)

(II)

wherein:

X, Y and Z are independently selected from the group consisting of N, CH and $CR^6$ wherein $R^6$ is halo, cyano, alkyl, substituted alkyl, heteroatom-containing alkyl (e.g., alkoxy, substituted alkoxy, or polyether) aryl, heteroaryl, substituted aryl, or substituted heteroaryl, or wherein two $R^6$ moieties on adjacent carbon atoms may be linked to form an additional cyclic group;

$Ar^1$ is as defined above;

$Ar^2$ and $Ar^3$ are independently selected from the group consisting of aryl, heteroaryl, substituted aryl and substituted heteroaryl containing one or two aromatic rings; and $R^2$ and $R^3$ are as defined above.

In formula (II), the polymer is a poly(phenylene vinylene) derivative when X, Y and Z are all CH. When at least one of X, Y and Z is N, the aromatic ring will be, for example, substituted or unsubstituted pyridinyl, pyridazinyl, pyrimidinyl, pyrazinyl, 1,2,4-triazinyl, or 1,2,3-triazinyl. Most preferably, one of X, Y and Z is CH and the other two are either CH or $CR^6$, wherein $R^6$ is alkyl, aryl, or heteroatom-containing alkyl, preferably alkoxy, and most preferably a polyether substituent —$(CH_2)_m(OCH_2CH_2)_p$OR wherein m, p and R are defined above.

The polymer may be a homopolymer or a copolymer with at least one additional type of monomer unit. Preferably, if the polymer is a copolymer, the additional monomer units are also arylene-vinylene monomer units, for example having the structure (III)

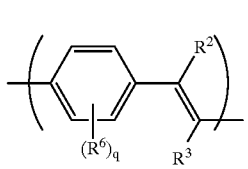

(III)

wherein $R^2$, $R^3$ and $R^6$ are as defined previously and q is an integer in the range of zero to 4 inclusive.

A particularly preferred polymer of the invention contains recurring monomer units having the structure of formula (IV)

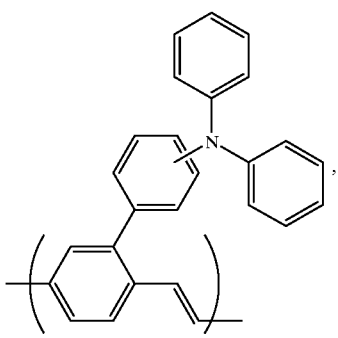

with the most preferred polymers encompassed by formula (IV) being poly(2-(4-diphenylaminophenyl)-1,4-phenylene vinylene and poly(2-(3-diphenylaminophenyl)-1,4-phenylene vinylene, as follows:

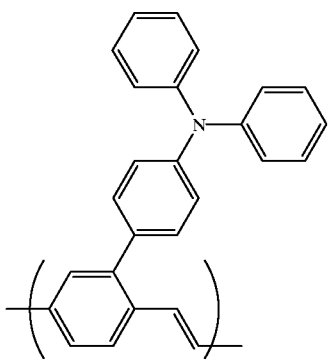

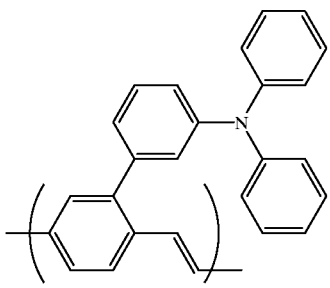

POLYMERIZATION

The arylamine-substituted arylene-vinylene polymers of the invention are generally synthesized by polymerizing monomers having the structure of formula (VI)

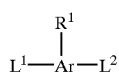

(VI)

wherein:

Ar and $R^1$ are as defined previously, and $L^1$ and $L^2$ are selected from the group consisting of —CHO, —Br, —I and —CH$_2$—L wherein L is a reactive group (e.g., a leaving group) that enables reaction with like monomers (i.e., also having the structure of formula (VI)) and/or with vinyl monomers. In the preferred polymers, such monomers have the structure of formula (VII)

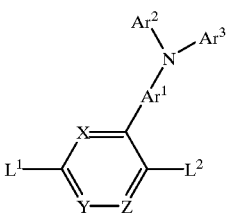

wherein X, Y, Z, $Ar^1$, $Ar^2$, $Ar^3$, $L^1$ and $L^2$ are as defined earlier. Preferred $L^1$ and $L^2$ groups will depend on the synthetic route chosen, but will generally be —CHO, —Br, —I or —CH$_2$—L wherein L is halo (particularly chloro), cyano, hydroxyl, lower alkoxy (e.g. methoxy), a lower alkyl ester (e.g., acetoxy), a phosphonium salt such as —PPh$_3^+$ Cl$^-$, other phosphorus moieties (e.g., —O—P(OCH$_2$CH$_3$)$_2$) or a sulfonium salt such as

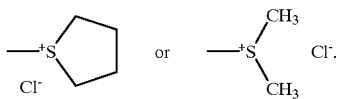

For example, the polymers of the invention may be prepared by dehydrochlorination coupling of the monomer (VIII)

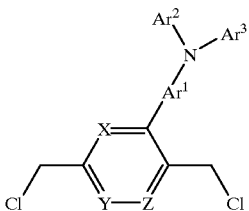

under reaction conditions typically used in the preparation of PPV. Such methodology will be known to those skilled in the art and is described in the pertinent literature and texts. Typically, this dehydrochlorination reaction involves use of a strong base such as lithium t-butoxide or sodium hydride and/or elevated temperatures (see Kraft et al. (1998) *Angew. Chem. Int. Ed.* 31:402–428).

The polymers may also be prepared by condensation of the aromatic dialdehyde (IX)

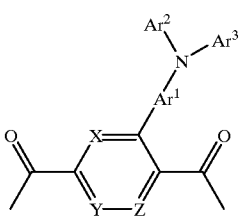

with the benzylic nitrile (X)

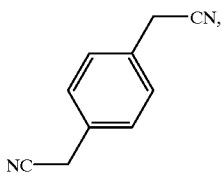
(X)

as described by Lahti et al. (1994) *Polymer* 3:1312, to give the polymer containing monomer units having the structure (XI)

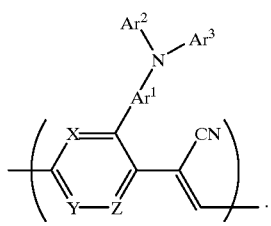
(XI)

The aromatic dialdehyde monomer (IX) may also be coupled to an aromatic bisphosphonium salt as initially described by McDonald (1960) *J. Am. Chem. Soc.* 8:4669 with respect to the synthesis of PPV.

Still another method for synthesizing the polymers of the invention involves polymerizing ethylene with the aromatic dibromide (XII)

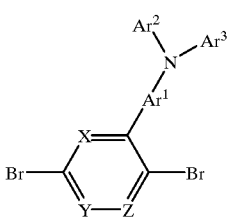
(XII)

via a Heck reaction, as described by Greiner et al. (1988) *Macromol. Chem., Rapid Commun.* 9:581, again with respect to the preparation of PPV.

The preferred method of synthesizing the polymers of the invention, however, employs the now-standard technique for preparing PPV commercially, involving initially forming the bis-sulfonium salt (XIII)

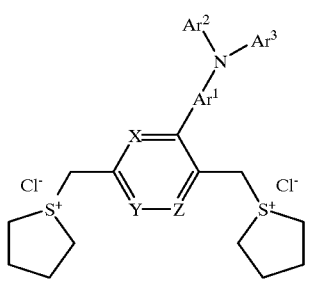
(XIII)

by treating the bis-dichloromethyl-substituted monomer (VIII) with tetrahydrothiophene. Polymerization of the bis-sulfonium salt (XIII) is induced by addition of a dilute base such as sodium hydroxide at low temperatures (e.g., 0 to 5° C.) in a suitable solvent (e.g., methanol) under an inert atmosphere, followed by conversion of the polymeric intermediate (XIV)

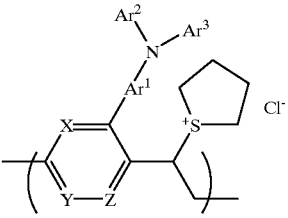
(XIV)

to the desired polymer using excess base and/or heat. See, e.g., Kraft et al., supra.

Preferred polymers herein have a number average molecular weight in the range of approximately 1000 to 2,000,000, and particularly preferred polymers have a number average molecular weight in the range of approximately 100,000 to 1,000,000.

As will be appreciated by those working in the field of conjugated polymers, the poly(arylene vinylenes) of the invention may be prepared by a host of other techniques not specifically described above. See, for example, Handbook of Conducting Polymers, 2$^{nd}$ Ed., Skotheim et al., Eds. (New York: Marcel Dekker, Inc., 1998), particularly Chapter 13, and references cited therein.

MONOMERIC PRECURSORS AND SYNTHESIS THEREOF

The monomers used to prepare the present polymers, i.e., compounds (VI) through (IX) and (XI) through (XIIp are novel compounds and are claimed as such herein. A particularly preferred method for synthesizing the novel monomers is illustrated in Scheme 1 and described in Example 1. In general, the monomers are synthesized by initially reacting a starting material having the structure of formula (XV)

$$L^3—Ar^1—NH_2 \tag{XV}$$

wherein $Ar^1$ is as defined earlier herein and $L^3$ is halo, preferably bromo, with at least one aromatic reactant $Ar^2—L^4$ wherein $Ar^2$ is as defined earlier and $L^4$ is halo, preferably iodo, to provide the arylamine intermediate (XVI)

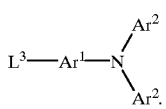
(XVI)

Intermediate (XVI) is then successively reacted with butyllithium and 2-isopropoxy-4,4,5,5-tetramethyl-1,3,2-dioxaborolane) to provide the dioxaboro-substituted intermediate (XVII)

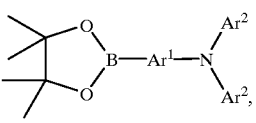
(XVII)

followed by reaction with a para-disubstituted aromatic ester having the structure (XVIII)

(XVIII)

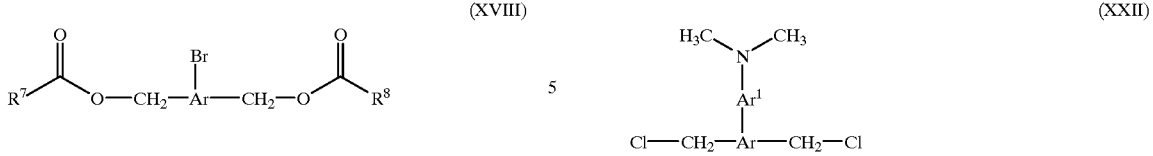

wherein Ar is as defined previously and $R^7$ and $R^8$ are independently lower alkyl, to provide the monomer (XIX)

(XIX)

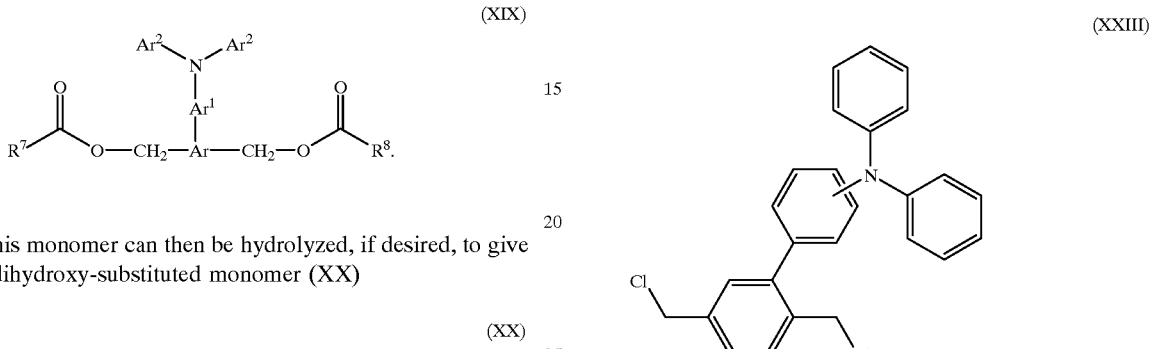

This monomer can then be hydrolyzed, if desired, to give the dihydroxy-substituted monomer (XX)

(XX)

which can in turn be converted to the bis-dichloromethyl terminated monomer (XXI) using a reagent effective to convert hydroxymethyl substituents to chloromethyl substituents, e.g., thionyl chloride.

(XXI)

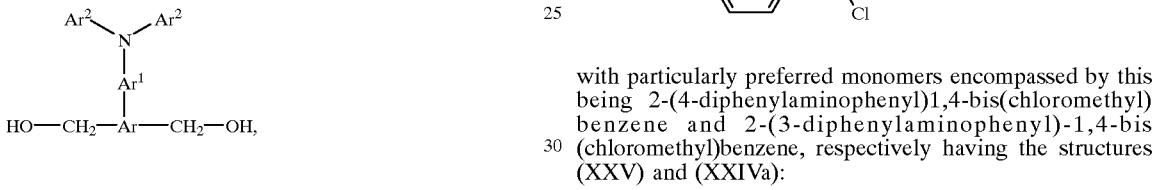

Those skilled in the art of synthetic organic chemistry will readily recognize that the aforementioned synthesis can be modified to provide a monomeric product having two different aryl substituents on the amino moiety by initially reacting the starting material (XV)

$L^3—Ar^1—NH_2$     (XV)

with two different aromatic reactants $Ar^2—L^4$ and $Ar^3—L^4$ rather than with a single aromatic reactant $Ar^2—L^4$ as described above. Further, the reactants $Ar^2—L^4$ and optionally $Ar^3—L^4$ may be replaced with reactants that are not necessarily aromatic, i.e., reactants such as $R^4—L^4$ and $R^5—L^4$ herein $R^4$ and $R^5$ are as defined earlier herein and may include a variety of hydrocarbyl, substituted hydrocarbyl, heteroatom-containing hydrocarbyl, or substituted heteroatom-containing hydrocarbyl substituents. For example, $R^4$ and $R^5$ may simply be methyl, giving rise to the monomer (XXII)

(XXII)

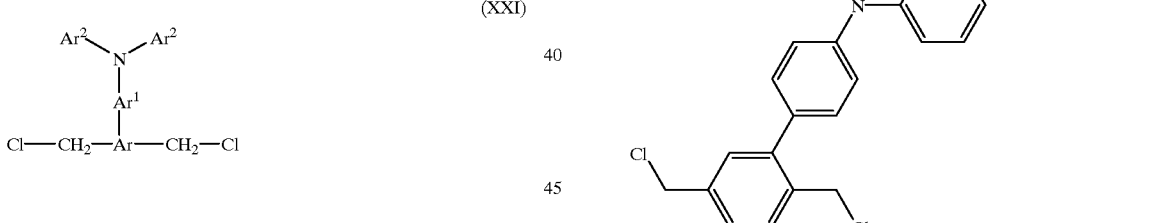

An exemplary monomer for use herein (see Example 1) has the structure of formula (XXIII)

with particularly preferred monomers encompassed by this being 2-(4-diphenylaminophenyl)1,4-bis(chloromethyl) benzene and 2-(3-diphenylaminophenyl)-1,4-bis (chloromethyl)benzene, respectively having the structures (XXV) and (XXIVa):

(XXIV)

(XXIV)

UTILITY

In general, the polymers of the invention are-useful in any application wherein a semiconductive polymer would have utility. Furthermore, upon being rendered conductive by doping or admixture with an ionizable species (e.g., using ion implantation), the polymers of the invention will find additional utility in those contexts wherein a conductive polymer would be useful.

Semiconductive compositions may be prepared that comprise a polymer of the invention optionally combined with an admixer, typically a compound selected such that charge and/or energy transfer takes place between the admixer and the polymer when a voltage is applied across the composition. For example, the admixer may be a second conjugated polymer, either an arylamine-substituted poly(arylene vinylene) as provided herein, or another type of conjugated polymer (e.g., selected from polyacetylene, polydiacetylene, polyparaphenylenes, polypyrroles, polythiophenes, polybithiophenes, polyisothianaphthenes, polyphenylenevinylenes, polythienylvinylenes, polyphenylenesulfides, and polyanilines), or some combination thereof. The admixer may also be a fullerene such as: $C_{60}$ itself ("Buckminsterfallerene"), having icosahedral symmetry and consisting of 12 five-membered rings and 20 six-membered rings; a higher order fullerene such as the ellipsoidally shaped $C_{70}$ and $C_{84}$, the icosahedrally shaped $C_{80}$ or $C_{140}$, or the giant, spherically shaped $C_{256}$; a hyperfullerene (or fullerene "onion") comprised of a concentric carbon cage that preferably contains $C_{60}$ (e.g., $C_{60}@C_{180}$, $C_{60}@C_{240}$, $C_{60}@C_{540}$, $C_{60}@C_{240}@C_{540}$); fullerene nanotubes; and fullerene capsules. Such semiconductive compositions may also advantageously contain one or more additional components, such as color modifiers, stability enhancers, crosslinking agents, ionizable species, phosphorescent dyes (as described, for example, by Baldo et al. (1998), "Highly Efficient Phosphorescent Emission from Organic Electroluminescent Devices," *Nature* 395:151–154), and the like.

Conductive compositions may be prepared by doping the polymers of the invention for conversion thereof to a conductive state. The term "doping" is used herein in its conventional sense to refer to the addition or withdrawal of electrons to a conjugated polymer so that positive or negative charge is introduced therein. Doping is thus essentially a redox reaction that involves electron transfer between a conjugated polymer and a dopant. Doping may be carried out electrochemically, by chemical treatment with a dopant (e.g., an oxidant dopant such as $AsF_5$, $FeCl_3$, iodine, $H_2SO_4$, $SO_3$, $HClO_4$, $CF_3COOH$, $H_2O_2$, etc.) or by other means, as will be appreciated by those skilled in the art. See, e.g., T. A. Skotheim et al., "*Electroresponsive Molecular and Polymeric Systems*," (New York: Marcel Dekker, 1991). Doping will generally be reversible, such that the conductive polymer can return to its original semiconductive state, or in some cases it may be permanent.

The polymers of the invention are particularly useful as electroluminescent materials (i.e., as materials that can generate light upon electrical excitation) in electroluminescence devices such as LEDs, photodetector devices, light-emitting electrochemical cells, and the like. Electroluminescence devices, including LEDs, are generally comprised of laminates of a suitable electroluminescent material disposed between a hole-injecting electrode layer and an electron-injecting electrode layer. Additional layers, elements, and/or a substrate may or may not be present. In a photodetector device, for example, a means for detecting a photocurrent (i.e., a light-induced electrical current) flowing between the electrodes will be included. Another use of the present polymers is in a photo voltaic device used for the generation of electrical power. Such devices generally comprise a first electrode, a semiconductive layer provided on the first electrode, and a second electrode (sometimes termed a "collector electrode") provided on the light incidence surface of the semiconductive layer; a polymer of the invention may be advantageously used as the aforementioned semiconductive layer. Electrochemical sensors may also be fabricated using the present polymers; such sensors are generally comprised of a counter electrode, a reference electrode, a working electrode, an optional reference electrode, and a means for applying an electrical potential between the working and counter electrodes, wherein a polymer of the invention is applied to the surface of the working electrode. The polymers are also useful in the fabrication of transistors, particularly field effect transistors. FETs, as is well known in the art, are comprised of a gate electrode, a source electrode, a drain electrode, and a semiconductive channel, e.g., comprising a polymer of the invention, electrically connecting the source electrode and the drain electrode.

A particularly preferred application of the present polymers is in the fabrication of an cavity-emission electroluminescent device as described in commonly assigned, co-pending U.S. patent application Ser. No. 09/618864 entitled "Cavity-Emission Electroluminescent Device and Method for Forming the Device" (Pei et al.), filed on even date herewith. The cavity-emission electroluminescent device is comprised of a layered structure having a hole-injection electrode layer for injecting holes into an electroluminescent material, an electron-injection electrode layer for injecting electrons into an electroluminescent material and a dielectric layer interposed between the hole-injecting and electron-injecting electrode layers. A cavity is formed extending through at least the dielectric layer and one of the electrode layers and has an interior cavity surface comprising a hole-injection electrode region, an electron-injection electrode region and a dielectric region. Once the cavity is formed, the interior cavity surface is coated with an electroluminescent coating material of the invention such that the electroluminescent material electrically contacts the hole-injection and electron-injection electrode regions of the surface.

Optionally, a plurality of cavities in an array may be formed in a layered structure to form an electroluminecent display device.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

EXPERIMENTAL

The practice of the present invention will employ, unless otherwise indicated, conventional techniques of polymer chemistry, and the like, which are within the skill of the art. Such techniques are explained fully in the pertinent texts and literature. See, e.g., *Vogel's Textbook of Practical Organic Chemistry*, $5^{th}$ Ed., B. S. Furniss et al., eds. (New York: Longman Scientific and Technical, 1989); A. Kraft et al. (1998) *Angew. Chem. Int.* Ed. 37:402–428; and T. A. Skotheim et al., "*Electroresponsive Molecular and Polymeric Systems*," (New York: Marcel Dekker, 1991), cited supra.

In the following examples, efforts have been made to ensure accuracy with respect to numbers used (e.g., amounts, temperature, etc.) but some experimental error and deviation should be accounted for. Unless indicated otherwise, temperature is in degrees C and pressure is at or near atmospheric. All solvents were purchased as-BPLC grade, and all reactions were routinely conducted under an inert atmosphere of argon unless otherwise indicated. All reagents were obtained commercially unless otherwise indicated.

EXAMPLE 1

Synthesis of 2-(4-diphenylaminophenyl)-1,4-bis(chloromethyl)benzene:

4-Diphenylamino-1-(4,4,5,5-tetramethyl-1,3,2-dioxaborolan-2-yl)benzene (6.09 g) was prepared by adding butyllithium (0.64 g dissolved in 4 mL hexane) was added into a solution of 4-bromotriphenylamine (3.24 g) in 50 mL tetrahydrofuran at −78° C. The mixture was stirred while the solution temperature warmed up to 10° C. It was cooled again to −78° C. when borolane (2.23 g) was added. The mixture was then stirred at room temperature for 20 hrs and poured into water. The product was extracted with ether, washed with brine, and dried with $MgSO_4$. Solvent was evaporated. The residue was chromatographed on a silica gel column using a hexane/ethyl acetate mixture as eluent (40:1). 2.03 g of the product, 4-diphenylamnino-1-(4,4,5,5-tetramethyl-1,3,2-dioxaborolan-2-yl)benzene, was obtained. Then, 4-diphenylamino-1-(4,4,5,5-tetramethyl-1,3,2-dioxaborolan-2-yl)benzene (6.09 g), 2-bromo-1,4-bis(acetyloxymethyl)benzene (4.9 g), tetrakis(triphenylphosphine)-palladium(0) (0.15 g), toluene (15 mL), and an aqueous solution of sodium carbonate (2M, 25 mL) were mixed under argon. The resulting mixture was stirred at reflux for 2 days, cooled, and poured into water. The aqueous mixture was then extracted with ether. The etheral solution was washed with dilute HCl, brine, dried with magnesium sulfate, and evaporated. The residue was recrystallized in methanol to yield 5.70 g of 2-(4-diphenylamnino-phenyl)-1,4-bis(acetyloxymethyl)benzene.

The resulting 2-(4-diphenylaminophenyl)-1,4-bis(acetyloxymethyl)benzene was hydrolyzed in a solution of sodium hydroxide (6 g) in ethanol/water (40 mL/20 mL). The resulting 2-(4-diphenylaminophenyl)-1,4-bis(hydroxymethyl)benzene was purified by recrystallization in toluene.

2-(4-Diphenylaminophenyl)-1,4-bis(hydroxymethyl)benzene (3.75 g) was reacted with excess amount of thionyl chloride in tetrahydrofuran. The crude product was recrystallized in hexanes to yield 1.5 g of 2-(4-diphenylaminophenyl)-1,4-bis(chloromethyl)benzene. $^1H$ NMR ($CDCl_3$): δ=4.6 (4H), δ=7.0–7.4 (8H,), δ=7.5–7.6 (1H).

In a similar manner, 2-(3-diphenylaminophenyl)-1,4-bis(chloromethyl)benzene was synthesized.

EXAMPLE 2

Synthesis of poly(2-(4-diphenylaminophenyl)-1,4-phenylene vinylene):

A potassium t-butoxide solution in tetrahydrofuran (1M, 2 mL) was added in 10 seconds into a solution of 2-(4-diphenylaminophenyl)-1,4-bis(chloromethyl)benzene (0.70 g) in 50 mL of tetrahydrofuran under argon and vigorous stirring at 22° C. After stirring at 22° C. for 10 minutes, the solution temperature was raised to refluxing. Then, more potassium t-butoxide solution in tetrahydrofuran (1M, 4 mL) was added, and the solution stirred and refluxed for 1.5 hrs. Methanol (100 mL) was added to terminate the reaction. The polymer that precipitated from the mixture was collected by filtration, washed repeatedly with methanol, water, water/methanol (1:1), and methanol. It was redissolved in chloroform, precipitated in methanol, and dried in vacuum to yield 0.43 g of bright yellow fibrous solid of poly(2-(4-diphenylaminophenyl)-1,4-phenylene vinylene). $^1H$ NMR ($CDCl_3$): δ=7.0–7.4 (broad peaks).

EXAMPLE 3

Synthesis of poly(2-(3-diphenylaminophenyl)-1,4-phenylene vinylene):

A potassium t-butoxide solution in tetrahydrofuran (1M, 2 mL) was added in 10 seconds into a solution of 2-(3-diphenylaminophenyl)-1,4-bis(chloromethyl)benzene (0.70 g) in 50 mL of tetrahydrofuran under argon and vigorous stirring at 22° C. After stirring at 22° C. for 10 minutes, the solution temperature was raised to refluxing. Then, more potassium t-butoxide solution in tetrahydrofuran (1M, 4 mL) was added, and the solution stirred and refluxed for 1.5 hrs. Methanol (100 mL) was added to terminate the reaction. The polymer that precipitated from the mixture was collected by filtration, washed repeatedly with methanol, water, water/methanol (1:1), and methanol. It was redissolved in chloroform, precipitated in methanol, and dried in vacuum to yield 0.41 g of bright yellow fibrous solid.

EXAMPLE 4

Synthesis of poly{[2-(4-diphenylaminophenyl)-1,4-phenylene vinylene)]-co-[2-(3-diphenylaminophenyl)-1,4-phenylene vinylene)]} (PMTPA-PPV):

A potassium t-butoxide solution in tetrahydrofuran (1M, 6 mL) was added in 10 seconds into a solution of 1,4-bis(chloromethyl)-2-(4-diphenylaminophenyl)benzene (0.35 g) and 1,4-bis(chloromethyl)-2-(3-diphenylaminophenyl)benzene (0.35 g) in 70 mL of 1,4-dioxane under argon and vigorous stirring at 95° C. The solution was stirred at reflux for 1 hr and cooled to 25° C. Methanol (100 mL) was added into the solution. The polymer that precipitated from the mixture was collected by filtration, washed repeatedly with methanol, water, water/methanol (1:1), and methanol. It was redissolved in chloroform, precipitated in methanol, and dried in vacuum to yield 0.35 g of bright yellow fibrous solid.

Figure 2:
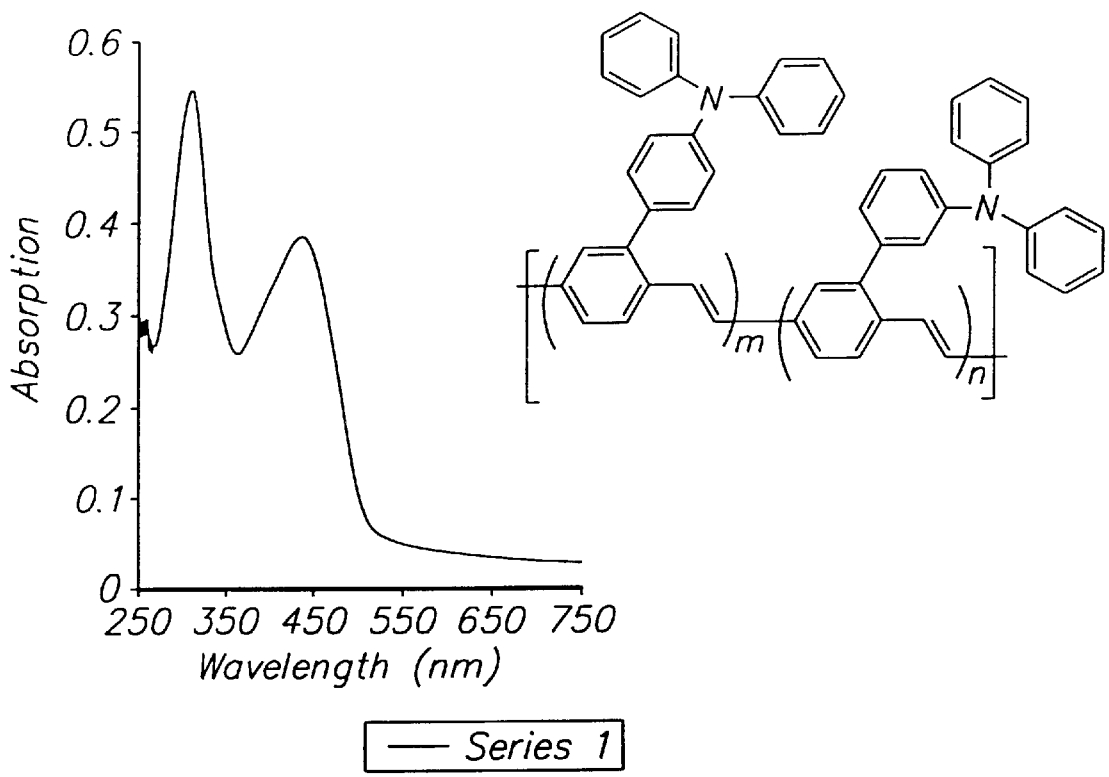
FIG. 2 shows the absorption spectrum of poly{[2-(4-diphenylaminophenyl)-1,4-phenylene vinylene)]-co-[2-(3-diphenylaminophenyl)-1,4-phenylene vinylene)]} ("PMTPA-PPV") in the ultraviolet-visible light wavelength range (see Example 4).
Figure 3:
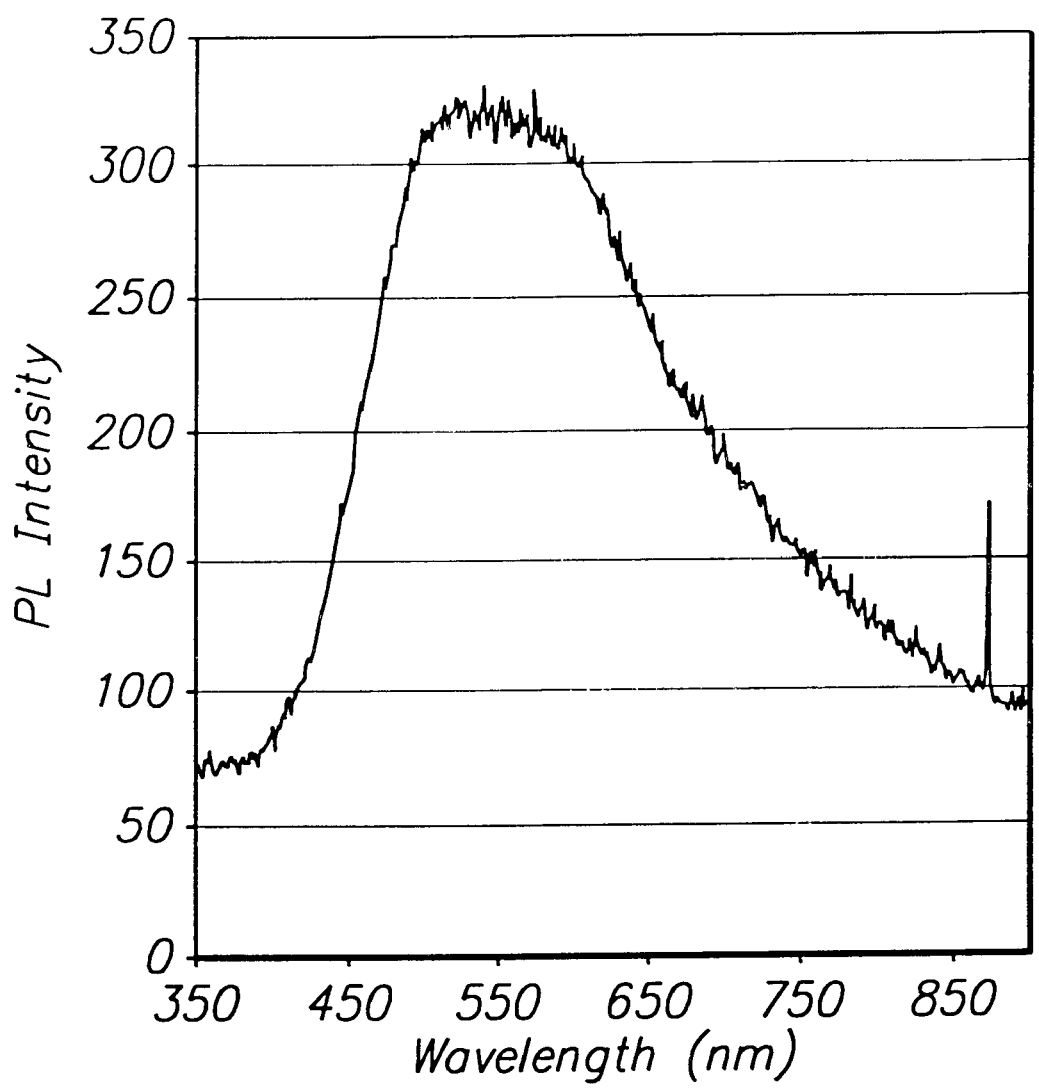
FIG. 3 shows the photoluminescent ("PL") spectrum of PMTPA-PPV thin films under the irradiation of an ultraviolet lamp (see Example 4).

Thin films of PMTPA-PPV were cast from its solution in chlorobenzene. FIG. 2 shows the chemical structure of PMTPA-PPV, as well as the absorption spectrum of the thin films in the ultraviolet-visible light wavelength range. FIG. 3 shows the photoluminescent spectrum of the thin films under the irradiation of a ultraviolet lamp. The sharp emission peak at around 860 nm is due to emission from the UV lamp.

EXAMPLE 5

Synthesis of poly{ [2-(4-diphenylaminophenyl)-1,4-phenylene vinylene)]-co-[2-methoxy-5-(2-ethylhexyloxy)-1,4-phenylene vinylene)]}:

A potassium t-butoxide solution in tetrahydrofuran (1M, 10 mL) was added in 10 seconds into a solution of 1,4-bis(chloromethyl)-2-(4-diphenylaminophenyl)benzene (0.5 g) and 1,4-bis(chloromethyl)-2-methoxy-5-(2-ethylhexyloxy)benzene (0.5 g) in 100 mL of 1,4-dioxane under argon and vigorous stirring at 95° C. The solution was stirred at reflux for 1 hr and cooled to 25° C. Methanol (100 mL) was added into the solution. The polymer that precipitated from the mixture was collected by filtration, washed repeatedly with methanol, water, water/methanol (1:1), and methanol. It was redissolved in tetrahydrofaran, precipitated in methanol, and dried in vacuum to yield 0.515 g of a bright orange fibrous solid.

EXAMPLE 6

Figure 4:
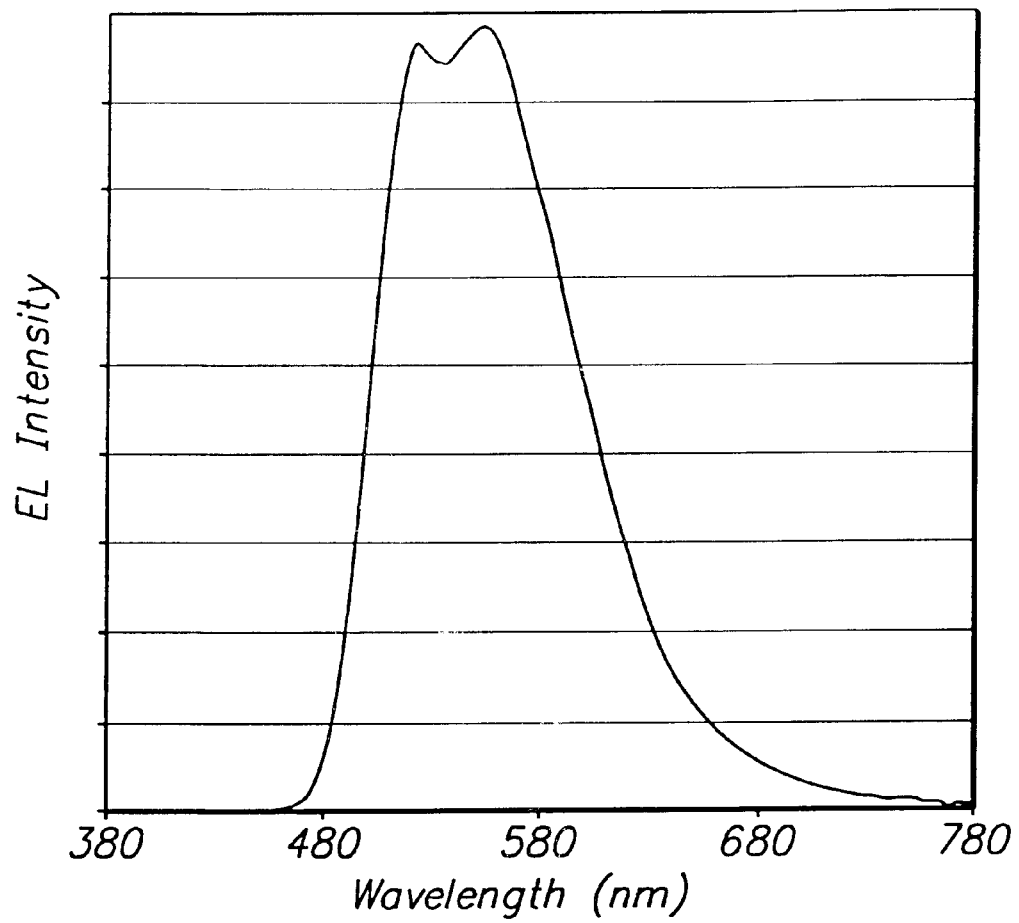
FIG. 4 shows the electroluminescent spectrum ("EL") of a PMTPA-PPV light-emitting layer of an LED, fabricated as described in Example 6.
Figure 5:
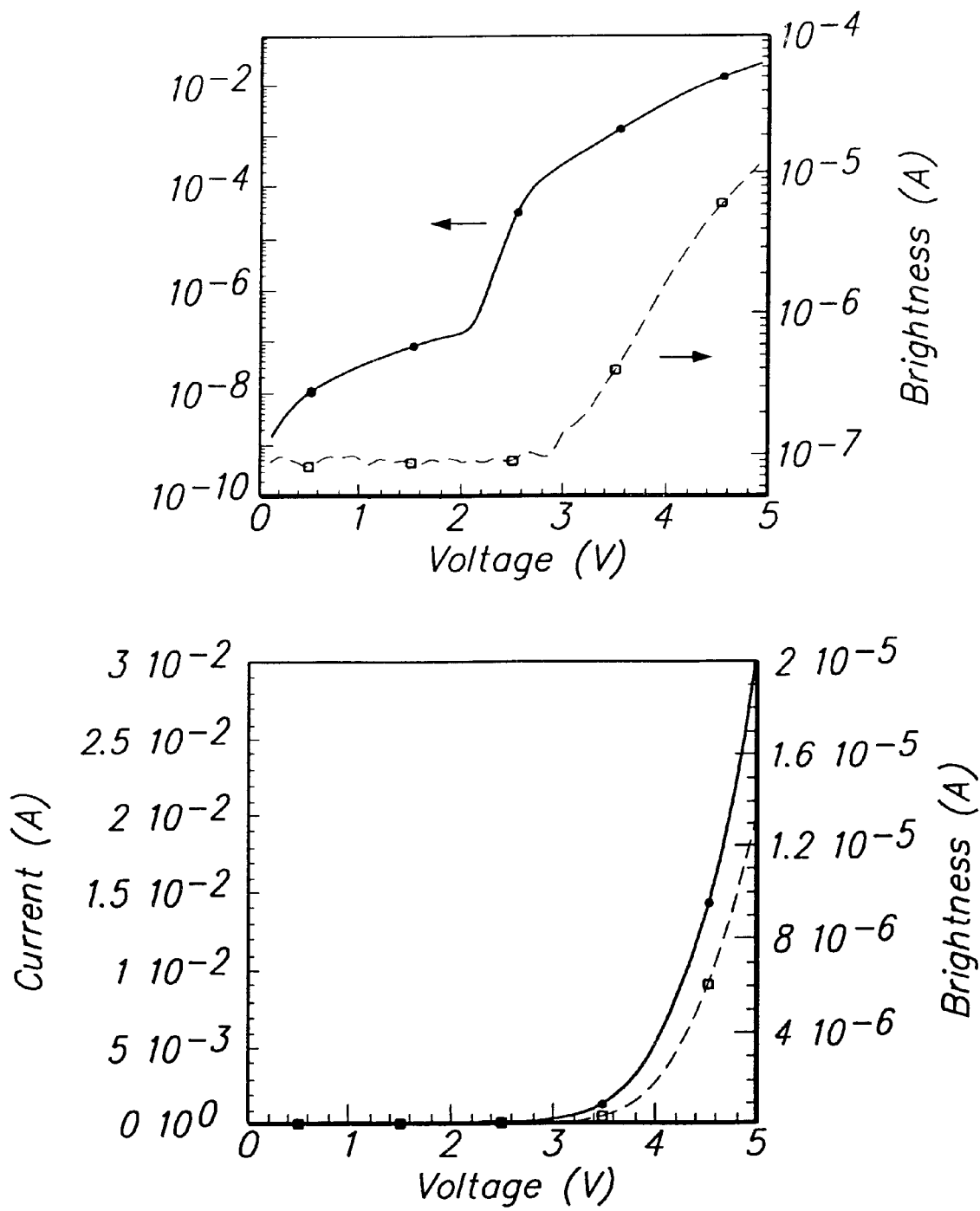
FIG. 5 shows current-light-voltage curves of the LEDs prepared and evaluated as described in Example 6.

Fabrication of Electroluminescent Diodes Based on PMTPA-PPV:

Light emitting diodes were fabricated on a transparent, indium-tin oxide (ITO) coated glass substrate. A thin layer of an aqueous dispersion of conducting poly(3,4-ethylenedioxythiophene)/poly(styrene sulfonic acid) was first spin-coated on ITO, followed by a thin film of PMTPA-PPV (800–2000 nm thick) from its solution in chlorobenzene. Then thin layers of calcium and aluminum were evaporated successively at pressures around $10^{-6}$ Torr. When a voltage (3–6 V) was applied between ITO and Al, light was emitted and visible through the ITO side. FIG. 4 shows the spectrum of the emitted light. This EL spectrum is similar to the PL spectrum shown in FIG. 3, indicating a similar luminescent process. FIG. 5 shows the current-light-voltage curves of the LEDs. The emission of light starts at around 3V and reaches 6500 cd/m$^2$ at 5V. The efficiency is around 2.8 cd/A.

What is claimed is:

1. A monomer suitable for preparing a conjugated arylene-vinylene polymer, having the structural formula (VI)

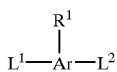

(VI)

wherein:

Ar is arylene, heteroarylene, substituted arylene or substituted heteroarylene containing one to three aromatic rings;

$R^1$ is an arylamine substituent having the formula —Ar$^1$—N(R$^4$R$^5$) wherein Ar$^1$ is as defined for Ar and R$^4$ and R$^5$ are independently selected from the group consisting of hydrocarbyl, substituted hydrocarbyl, heteroatom-containing hydrocarbyl, and substituted heteroatomkin containing hydrocarbyl, or R$^4$ and R$^5$ together form a cyclic group; and L$^1$ and L$^2$ are selected from the group consisting of —CHO, —Br, —I and —CH$_2$—L wherein L is a reactive group that enables reaction with like monomers.

2. A monomer suitable for preparing a conjugated arylene-vinylene polymer, having a the structural formula (VII)

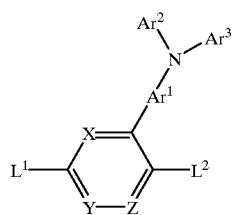

(VII)

wherein:

X, Y and Z are independently selected from the group consisting of N, CH and CR$^6$ wherein R$^6$ is halo, cyano, alkyl, substituted alkyl, heteroatom-containing alkyl, aryl, heteroaryl, substituted aryl, or substituted heteroaryl, or wherein two R$^6$ moieties on adjacent carbon atoms may be linked to form an additional cyclic group;

Ar$^1$ is arylene, heteroarylene, substituted arylene or substituted heteroarylene containing one to three aromatic rings;

Ar$^2$ and Ar$^3$ are independently selected from the group consisting of aryl, heteroaryl, substituted aryl and substituted heteroaryl containing one or two aromatic rings; and L$^1$ and L$^2$ are selected from the group consisting of —CHO, —Br, —I and —CH$_2$—L wherein L is a reactive group that enables reaction with like monomers.

3. The monomer of claim 1, wherein X, Y and Z are all CH.

4. The monomer of claim 1, wherein at least one of X, Y and Z is N.

5. The monomer of claim 1, wherein at least one of X, Y and Z is CR$^6$ and R$^6$ is heteroatom-containing alkyl.

6. The monomer of claim 5, wherein R$^6$ is alkoxy.

7. The monomer of claim 5, wherein R$^6$ is a polyether substituent.

8. The monomer of claim 1, wherein Ar$^1$ is phenylene and Ar$^2$ and Ar$^3$ are both phenyl.

9. The monomer of claim 1, wherein L$^1$ and L$^2$ are both —CH$_2$—L and L is selected from the group consisting of halo, hydroxyl, lower alkoxy, and lower alkyl esters.

10. The monomer of claim 9, wherein L$^1$ and L$^2$ are the same, and L is halo.

11. The monomer of claim 10, wherein L is chloro.

12. The monomer of claim 2, wherein L$^1$ and L$^2$ are —CH$_2$—L and L is selected from the group consisting of halo, hydroxyl, lower alkoxy, and lower alkyl esters.

13. The monomer of claim 12, wherein L$^1$ and L$^2$ are the same, and L is halo.

14. The monomer of claim 13, wherein L is chloro.

15. The monomer of claim 2, wherein Ar$^1$ is phenylene and Ar$^2$ and Ar$^3$ are both phenyl.

16. A monomer suitable for preparing a conjugated arylene-vinylene polymer, selected from the group consisting of 2-(4-diphenylaminophenyl)-1,4-bis(chloromethyl)benzene and 2-(3-diphenylaminophenyl)-1,4-bis(chloromethyl)benzene.

* * * * *

UNITED STATES PATENT AND TRADEMARK OFFICE
CERTIFICATE OF CORRECTION

PATENT NO.     : 6,372,881 B2
DATED          : April 16, 2002
INVENTOR(S)    : Qibing Pei It is certified that error appears in the above-identified patent and that said Letters Patent is hereby corrected as shown below:

Column 21,
Line 39, delete "heteroatomkin" and insert -- heteroatom --.
Line 46, delete "having a the" and insert -- having the --.

Column 22,
Lines 24, 26, 29 and 35, delete "claim 1" and insert -- claim 2 --.

Signed and Sealed this

Tenth Day of December, 2002

JAMES E. ROGAN
*Director of the United States Patent and Trademark Office*

UNITED STATES PATENT AND TRADEMARK OFFICE
CERTIFICATE OF CORRECTION

PATENT NO.     : 6,372,881 B2                                                          Page 1 of 1
DATED          : April 16, 2002
INVENTOR(S)    : Qibing Pei It is certified that error appears in the above-identified patent and that said Letters Patent is hereby corrected as shown below:

<u>Title page,</u>
After Item [73], entitled "Assignee" please add the following new section:

-- REFERENCE TO GOVERNMENT SUPPORT
This invention was funded in part by the United States Office of Naval Research under Contract No. N00014-99-C-0274. The United States Government has certain rights in this invention. --

Signed and Sealed this

Nineteenth Day of August, 2003

JAMES E. ROGAN
*Director of the United States Patent and Trademark Office*